United States Patent [19]

Bloom

[11] Patent Number: 4,944,737
[45] Date of Patent: Jul. 31, 1990

[54] SURGICAL STENCIL AND METHOD OF USING THE SAME

[75] Inventor: Robert F. Bloom, Lubbock, Tex.

[73] Assignee: Kathryn Rowe Bloom, Lubbock, Tex.

[21] Appl. No.: 284,333

[22] Filed: Dec. 14, 1988

[51] Int. Cl.⁵ .............................................. A61B 19/00
[52] U.S. Cl. ...................................... 606/1; 128/898; 33/565
[58] Field of Search ................... 128/303 R, 305, 898; 33/562, 563, 566, 565; 606/1

[56] References Cited

U.S. PATENT DOCUMENTS

| 4,192,312 | 3/1980 | Wilson | 128/303 R |
| 4,279,259 | 7/1981 | Lee et al. | 128/774 |

Primary Examiner—Michael H. Thaler
Attorney, Agent, or Firm—Wendell Coffee

[57] ABSTRACT

A clear plastic sheet has drawn thereon, the excision necessary to remove a skin defect and also drawn thereon, lines indicating the incisions necessary to make a flap. The transparent sheet is placed over the defect to orient the flap location. Perforations along the lines in the clear plastic sheet permit the skin to be marked so that the drawing on the sheet may be reproduced upon the skin.

4 Claims, 2 Drawing Sheets

© 1988 Robert Bloom

© 1988 Robert Bloom

SURGICAL STENCIL AND METHOD OF USING THE SAME

RIGHTS TO INVENTIONS, ETC.

There was no federally sponsored research and development concerning this invention.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever (1077 OG 22).

BACKGROUND OF THE INVENTION (1) Field of the Invention

This invention relates to surgery, and more particularly to skin surgery and local flaps. A plastic surgeon is one having ordinary skill in this art.

(2) Description of the Related Art

Local skin flaps have been known for many years. A flap of skin is moved from one location to another location. The donor tissue is obtained from the area adjacent to the defect and is not detached from the body but merely moved, always being attached to other tissue. Stated otherwise, when some skin is removed along with a skin defect, then a flap of skin adjacent to it is moved to cover where the defect was removed.

Although the basic concept is simple, the practice requires considerable knowledge of geometry, skin biomechanics, and in the case of facial surgery, knowledge of facial anatomy combined with a sense of aesthetics and an appreciation for shapes, symmetry, and color (see page 3 of Ian T. Jackson's *Local Flaps in Head and Neck Reconstruction*, copyrighted and published in 1985 by The C. V. Mosby Company, St. Louis, Toronto, and Princeton).

One of the basic considerations is to obtain a flap of the approximate size of the defect to be covered and to move it there. If the skin is stretched beyond safe limits, there is likely to be a compressed circulation with disastrous results. Also, the skin over the defect, itself, should probably be stretched as little as possible, although there obviously must be some stretching of skin in the general area. This requires that the area of the defect should be inspected to determine the best position for the flap placement. Generally, if an attempt is made to use a small flap to fill a big hole, there will be a loss of the flap. Also, if there is an attempt to extend the flap outside of its blood supply, there will be a failure and a loss of the flap.

Jackson, in his book identified above, suggests that often times that a piece of gauze is used to assess whether a flap will do what is required (pg. 8, Jackson, supra).

The book identified above describes many of the basic type of flaps and the basic geometry for them, e.g., the rotation flap (beginning of page 7), the transposition flap (beginning of page 10), the advancement flap (page 12), the island technique (page 14), and then specific types such as the rhomboid (Limberg) flap (page 16), the dufourmentel flap (Lambeau En L Pour Losange, "LLL" flap) (page 20), as well as the bilobed flap (page 21).

BLISS, U.S. Pat. No. 4,576,163 discloses a surgical implement which is pressed against the skin to leave a mark on the skin to indicate where it would be desirable to remove a defect and close the skin removed with a small hairline scare. This device is a rigid metal device that would produce one pattern for one size incision.

WILSON, U.S. Pat. No. 4,192,312 discloses a patch-like sheet of material adapted to be placed over skin tumors for aiding the surgeon or making the optimum size and shape incision for removing the tumor. A sheet of material was provided with openings, as is understood, the sheet of material would be attached as by adhesion to the skin, and there would be a removal of all or part of the patch along with the skin tumor and surrounding skin.

LEE, U.S. Pat. No. 4,279,259 discloses a mammometer for making measurements of mammary glands for doing breast surgery. The meter would have certain holes and openings therein for marking the skin.

SUMMARY OF THE INVENTION (1) Progressive Contribution to the Art

This invention concerns a surgical stencil to aid the surgeon in making the right size and shape excision, and also to aid the surgeon in determining the size of the flap, the area from which to obtain the flap material so the surgeon has a better idea of where the skin will be stretched, and if the stretching of the skin will interfere with facial landmarks such as hairlines or eyebrows and the like.

Once the surgeon has determined the size of an excision and the orientation of the flap, he readily marks the skin with the outlines of where each incision will be made, not only to remove the skin defect, but also to produce the flap that will be used to cover the hole in the skin caused by the removal of the defect. This is done by different sized closed figures drawn on a sheet of transparent material, and also the flap outlines drawn for each of and different figures. Perforations through the sheet permit the excision lines and incision lines to be drawn on the skin.

(2) Objects of this Invention

An object of this invention is to remove skin defects and cover the area with a local flap.

Further objects are to achieve the above with devices that are sturdy, compact, durable, lightweight, simple, safe, efficient, versatile, ecologically compatible, and reliable, yet inexpensive and easy to manufacture, use and maintain.

Other objects are to achieve the above with a method that is rapid, versatile, ecologically compatible, efficient, and inexpensive, and does not require special extensive training to use and maintain.

Further objects are to achieve the above with a product that is easy to store, has a long storage life, is safe, versatile, efficient, stable and reliable, yet is inexpensive and easy to manufacture.

The specific nature of the invention, as well as other objects, uses, and advantages thereof, will clearly appear from the following description and from the accompanying drawing, the different views of which are not scale drawings.

Figure 1:
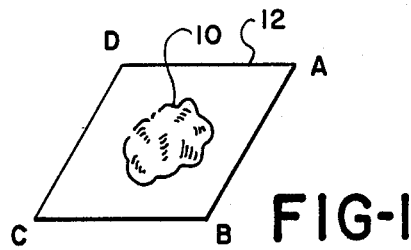
FIG. 1 shows an example of the prior art of a defect with the excise lines for making a rhomboid excision thereof.

As an aid to correlating the terms of the claims to the exemplary drawing, the following catalog of elements and steps is provided:

10 defect
12 rhomboid
14 hole
16 incision
18 incision
20 flap
30 sheet
32 small rhomboid
34 medium small rhomboid
36 medium large rhomboid
38 large rhomboid
40 perforation
42 perforation
50 dot, skin
52 dot, skin
62 small line for cut 16
64 medium small line for cut 16
66 medium large line for cut 16
68 large line for cut 16
82 small line for cut 18
84 medium small line for cut 18
86 medium large line for cut 18
88 large line for cut 18

DESCRIPTION OF THE PREFERRED EMBODIMENT:

Referring to the drawings, FIGS. 1-4 show the prior art and are basically reproduced from page 17 of Jackson's *Local Flaps in Head and Neck Reconstruction*. There may be seen a skin defect 10 represented in FIG. 1 with rhomboid closed FIG. 12. The rhomboid closed figure will have the four angles designated as A, B, C, and D.

Figure 2:
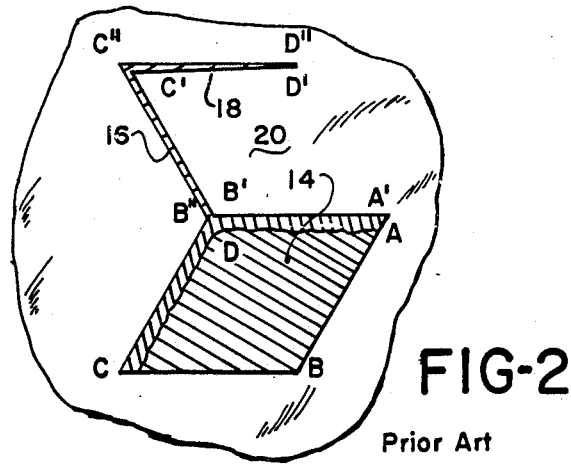
FIG. 2 shows the hole created by the excision of FIG. 1 with the incisions for a flap according to the prior art.

FIG. 2 shows the condition of the skin after the defect has been excised leaving a rhomboid shaped hole 14 and incision cuts 16 and 18 to form flap 20. The angles or corners of the rhomboid hole are again designated by the letters A, B, C, and D Also, the corners or angles of the flap have been designated as A', B', C', and D' for reasons which will appear later. Likewise, the skin "outside" of the flap has been designated at its corners as B", C", and D".

Figure 3:
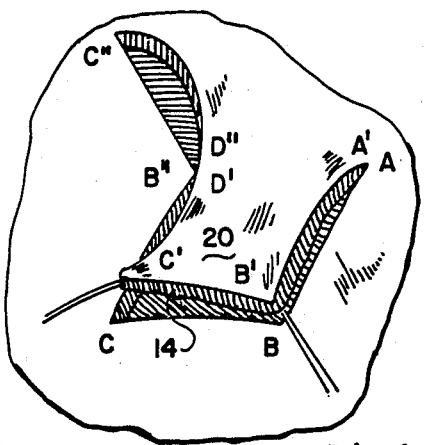
FIG. 3 shows the moving of a flap of skin to cover the excision of FIG. 1.

FIG. 3 shows the flap having been moved into position over the hole. It will be noted that the portion of the flap which will cover the hole 14 will be moved. Therefore, it is necessary that the skin at the flap 20 and some surrounding skin be free from the flesh beneath it. This will probably require the skin to be undercut so that it is free to move.

FIG. 3 shows the flap 20 moved over the hole 14 before suturing. It may be seen in this position, that there is considerable stretching and movement of the skin of the flap. However, close examination will show that the incision 16 from B' to C' is the same length of each of the sides of the rhomboid. I.e., the length of the flap from B' to C' is the same length as the side of the rhomboid B to C. The flap distance from C' to D' is the same length as the hole rhomboid side C to D. Likewise, the distance of the flap from A' to D' is the same as the side of the rhomboid from A to D. I.e., the skin represented in the flap 16 has not been stretched, although it has been moved. The skin away from the flap has been stretched.

Figure 4:
FIG. 4 shows the completed flap as in the prior art.

FIG. 4 shows the site after the flap 20 has been secured by sutures.

Experience in skin flap has shown the desirability of not stretching the skin of the flap itself but permitting the stretching of the skin away from the flap results in more successful use of local flaps. However, since the sizing of the excision to produce the hole 14 and the incisions 16 and 18 to produce the flap 20 need to be rather precise, it can be seen that this is placing considerable requirements upon the surgeon without some aid.

Figure 5:
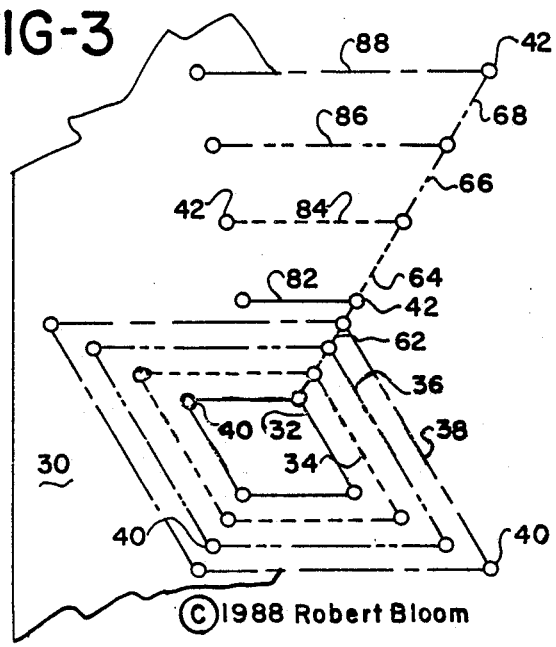
FIG. 5 is an illustration of a stencil according to this invention to be used in the flap surgery as shown in FIGS. 1-4.

FIG. 5 shows such an aid.

A series of concentric, similar geometric figures are drawn or depicted or delineated upon clear plastic sheet 30. Specifically, there is shown small rhomboid 32 with solid lines, medium small rhomboid 34 with broken lines, medium large rhomboid 36 with a double dot line, and large rhomboid 38 with a single dot line. For black and white representation, the lines have been shown either solid or broken as described for different designations. On the clear plastic sheet 30, I prefer to use different colors of line.

It may be seen that each of the rhomboids are similar. I.e., all the sides of each rhomboid are equal and all of the rhomboids have 60° and 120° angles. It will be understood particularly by those skilled in the art and from a study of the Jackson text, that there are other closed geometric figures which might be used which are sometimes designated as diamonds, triangles, circles, or ellipsis.

Figure 7:
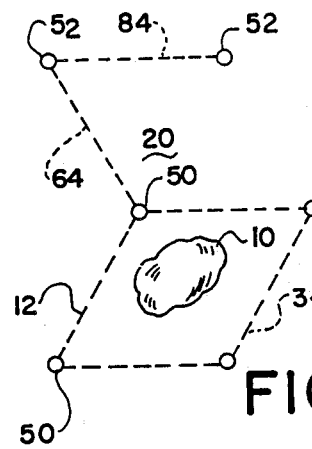
FIG. 7 is an illustration of the skin marked from the stencil with the dashed lines used for clarity of illustration.

Each of the rhomboids 32-38 have a perforation 40 at each angle thereof which will be at each of the ends of each line. Therefore, when the clear plastic sheet 30 is placed over the skin having the defect 10, and the size of the excision has been determined, then the skin may be marked with a skin marker through the four perforations indicating a corner of the rhomboid. Such a mark on the skin is shown in FIG. 7 with each of the corners being marked by dot 50.

For each rhomboid 32-38 upon the clear plastic sheet 30, there are shown or depicted or delineated at least one incision line corresponding thereto. For the particular flap of the rhomboid flap, there are two, one corresponding to the incision 16 and one corresponding to the incision 18. I.e., for the large rhomboid, there has been depicted the incision line 88 designated corresponding to incision 18, and also incision line 68 corresponding to incision line 16. Likewise, for the medium small rhomboid 34, there has been indicated an incision line 84 corresponding to incision 18 of FIG. 2, and also an incision line 64 corresponding to incision line 16. There are also flap incision lines for the small rhomboid 32 and the medium large rhomboid 36. At the termination of each line (technically line segment), there is a perforation 42 so that a skin marker through the perforation can mark the terminations of these lines upon the skin, as seen by dot 52 in FIG. 7.

Figure 6:
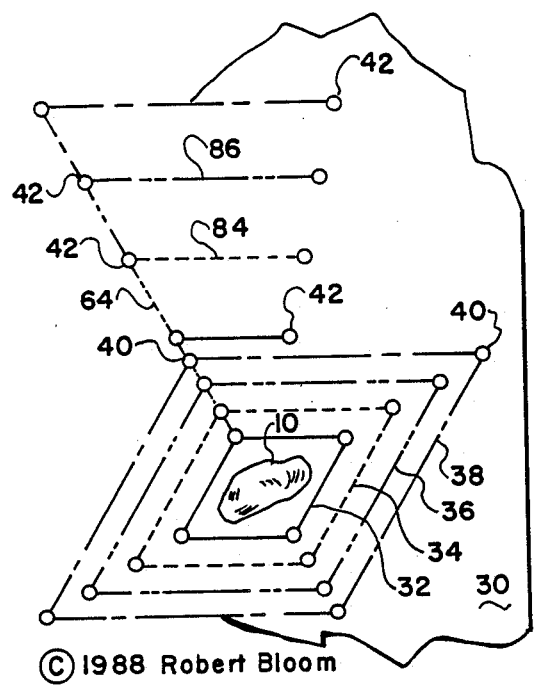
FIG. 6 is an illustration of the stencil (inverted from FIG. 5) over the skin defect.

To use this invention, the surgeon first determines the shape of the excision to be made. This would not be an irreversible decision. E.g., the surgeon would first select as to whether it would be a triangle excision or a rhomboid excision. Then, he would select one of the clear plastic sheets 30 with a plurality of concentric closed geometric figures thereon. I.e., if he decided to have a rhomboid excision, he would select the sheet 30 having a plurality of rhomboids 32, 34, 36, and 38 thereon. He would then place that figure over the defect to be excised, as seen in FIG. 6. He would next decide as to which size of the concentric rhomboid figures to be used. In the drawing, it is shown that a medium small rhomboid 34 would be selected.

The surgeon would also rotate the sheet 30 with the defect 10 centered within the closed figures to see what position was most desirable. The surgeon would also invert (as between FIGS. 5 and 6) the sheet 30 for the most desirable flap 20 position. This would take into consideration particularly where the flap 20 would be produced from, and where the skin would be stretched, where the skin would be undercut, as well as the color, etc. of the skin.

When the surgeon had decided upon the size of the excision 12 and the location of the flap 20 he would then use a skin marker to make dots 50 and 52 upon the skin as appropriate and as seen in FIG. 7. Then he would put the stencil aside and proceed with the surgery as shown in FIGS. 2-4 as is well known to the local flap cosmetic surgery arts.

The embodiment shown and described above is only exemplary. I do not claim to have invented all the parts, elements or steps described. Various modifications can be made in the construction, material, arrangement, and operation, and still be within the scope of my invention.

The restrictive description and drawing of the specific examples above do not point out what an infringement of this patent would be, but are to enable one skilled in the art to make and use the invention. The limits of the invention and the bounds of the patent protection are measured by and defined in the following claims.

I claim as my invention:

1. The method of performing flap surgery at a site on skin comprising:
   a. selecting a shape of excision from a plurality of shapes of excision, then
   b. placing on the site a transparent stencil having lines and perforations depicting a plurality of sizes of the selected shape of excision and incision lines for flaps for each excision size.

2. The method of performing flap surgery at a site on skin comprising:
   a. selecting a shape of excision, then
   b. placing on the site a transparent stencil having lines and perforations depicting a plurality of sizes of the selected shape of excision and incision lines for flaps for each excision size,
   c. selecting the orientation of the flap by rotating said stencil with the drawing over the site,
   d. selecting the size of excision by holding the stencil with the drawing of the excisions over the site, thereafter
   e. marking the skin with the size of the selected shape through perforations in the stencil, and
   f. marking the skin with the location of the incision for the flap through perforation in the stencil.

3. A surgical stencil for use in performing flap surgery comprising:
   a. a clear sheet of plastic,
   b. lines depicting at least two concentric closed geometric figures thereon representing the excisions to be made to remove a skin defect,
   c. at least one additional line connected to each of the closed figures representing the incision to be made in the skin to produce a local flap to cover a hole in the skin made by an excision following the lines of one of the closed geometric figures,
   d. a perforation through the clear plastic sheet at each end of each of the lines, so that
   e. the skin may be marked with sufficient dots that one of the closed geometric figure can be reproduced upon the skin and also an incision line from the stencil may be reproduced upon the skin.

4. The invention as defined in claim 3 wherein:
   f. the lines of each closed figure and its flap line are distinctly different from the lines of different closed figures and their flap lines upon the same transparent sheet.

* * * * *